US010946179B2

(12) United States Patent
Napolez

(10) Patent No.: US 10,946,179 B2
(45) Date of Patent: Mar. 16, 2021

(54) GASTROSTOMY TUBE REINSERTION DEVICE

(71) Applicant: Adolfo Napolez, Flossmoor, IL (US)

(72) Inventor: Adolfo Napolez, Flossmoor, IL (US)

( * ) Notice: Subject to any disclaimer, the term of this patent is extended or adjusted under 35 U.S.C. 154(b) by 0 days.

(21) Appl. No.: 16/331,523

(22) PCT Filed: Aug. 4, 2017

(86) PCT No.: PCT/US2017/045548

§ 371 (c)(1),
(2) Date: Mar. 7, 2019

(87) PCT Pub. No.: WO2018/048538

PCT Pub. Date: Mar. 15, 2018

(65) Prior Publication Data

US 2019/0201670 A1 Jul. 4, 2019

Related U.S. Application Data

(60) Provisional application No. 62/384,885, filed on Sep. 8, 2016.

(51) Int. Cl.
*A61M 29/00* (2006.01)
*A61J 15/00* (2006.01)
*A61B 17/34* (2006.01)

(52) U.S. Cl.
CPC ......... *A61M 29/00* (2013.01); *A61B 17/3415* (2013.01); *A61J 15/0015* (2013.01); *A61M 2205/0222* (2013.01)

(58) Field of Classification Search
CPC .............. A61B 17/3415; A61J 15/0015; A61J 15/0019; A61J 15/0023; A61M 29/00
See application file for complete search history.

(56) References Cited

U.S. PATENT DOCUMENTS 4,668,225 A 5/1987 Russo et al.
4,758,219 A 7/1988 Sacks et al.
5,080,650 A 1/1992 Hirsch et al.
(Continued)

FOREIGN PATENT DOCUMENTS

WO 02083013 A1 10/2002

OTHER PUBLICATIONS

International Search Report and Written Opinion of the International Searching Authority issued by the U.S. Patent Office dated Dec. 15, 2017 for PCT/US2017/045548.
(Continued)

*Primary Examiner* — Jan Christopher L Merene
(74) *Attorney, Agent, or Firm* — Jennifer S. Stachniak, Esq.; Johnson, Marcou, Isaacs & Nix, LLC

(57) ABSTRACT

The invention disclosed herein is a gastrostomy tube reinsertion device. The present invention provides a dilation device for dilating the gastrostomy tube tract in living tissues. In one aspect, the gastrostomy tube reinsertion device comprises multiple dilators to open collapsed soft tissue within the gastrostomy tube tract. Such device is useful for reinserting a gastrostomy tube into the previously defined tract in a human body, even after partial closure of the tract and gastrostomy tube insertion site. In another aspect, the present invention provides the method or steps for reinserting a gastrostomy tube into a patient.

9 Claims, 2 Drawing Sheets

(56) References Cited

U.S. PATENT DOCUMENTS

| | | | | | |
|---|---|---|---|---|---|
| 5,807,314 | A | 9/1998 | Ross et al. | | |
| 5,860,952 | A | 1/1999 | Quinn | | |
| 2002/0087152 | A1 * | 7/2002 | Mikus | A61B 18/02 | 606/21 |
| 2002/0133128 | A1 | 9/2002 | Heller | | |
| 2002/0193822 | A1 * | 12/2002 | Hung | A61B 17/3439 | 606/198 |
| 2003/0083689 | A1 * | 5/2003 | Simonson | A61B 17/025 | 606/191 |
| 2004/0147877 | A1 * | 7/2004 | Heuser | A61M 25/0662 | 604/165.02 |
| 2005/0171541 | A1 * | 8/2005 | Boehm, Jr. | A61F 2/4465 | 623/17.16 |
| 2005/0234497 | A1 * | 10/2005 | Hung | A61M 29/00 | 606/191 |
| 2006/0004398 | A1 * | 1/2006 | Binder, Jr. | A61M 29/00 | 606/191 |
| 2006/0030872 | A1 | 2/2006 | Culbert | | |
| 2009/0137870 | A1 | 5/2009 | Bakos | | |
| 2012/0302837 | A1 | 11/2012 | Griffith | | |
| 2018/0021059 | A1 * | 1/2018 | Dolgin | A61M 25/0009 | 600/204 |

OTHER PUBLICATIONS

Kejariwal, Deepak et al., "Cut and Push Method of Percutaneous Endoscopic Gastrostomy Tube Removal in Adult Patients: The Ipswich Experience", Nutr Clin Pract, 24:28, 2009.

"Invitation to Pay Additional Fees" issued by the United States Patent and Trademark Office, as International Searching Authority dated Oct. 10, 2017 for PCT International Application No. PCT/US2017/045548.

"Extended European Search Report" issued by the European Patent Office (EPO) dated Mar. 11, 2020 for counterpart European Application No. 17849261.7.

* cited by examiner

GASTROSTOMY TUBE REINSERTION DEVICE

TECHNICAL FIELD

The invention relates generally to a gastrostomy tube reinsertion device. More specifically, the present invention is related to a method and device for progressive dilation of the gastrostomy tube site for purposes of reinserting a new gastrostomy tube in the event the tube is removed or dislodged from the patient's body. In addition, the present invention is related to a gastrostomy tube reinsertion kit for the purposes of reinserting a new gastrostomy tube in the patient's body.

BACKGROUND

A gastrostomy tube is a medical device used to provide nutrition to patients who cannot obtain nutrition by mouth, are unable to swallow, or need nutritional supplementation. The placement of a gastrostomy tube may be temporary for the treatment of acute conditions or lifelong for patients with chronic disabilities. Gastrostomy tubes are placed in patients of all age groups and disease states to permit nutrition, fluids, and medications to be placed directly into the stomach, when oral intake is not possible.

During the initial placement of the gastrostomy tube, a tract or stoma is formed in the stomach and a tube is placed through the tract or stoma. This surgical opening and/or the procedure to create the opening is commonly referred to as gastrostomy. Feeding solutions can be injected through the gastrostomy tube directly into the stomach to provide nutrients to the stomach, known as enteral feeding. A variety of different gastrostomy tubes intended for enteral feeding have been developed over the years. There are gastrostomy tubes having a low profile relative to the portion of the tube, which sits on a patient's skin, as well as those having a more traditional profile or non-low profile configuration.

There are a variety of gastrostomy devices used in medical practice. The gastrostomy tubes are usually made of polyurethane or silicone. The diameter of a gastrostomy tube is measured in French units (each French unit equals 0.33 millimeters). The average gastrostomy tube is 20 French units in diameter. The gastrostomy tubes are frequently used in a procedure called percutaneous endoscopic gastrostomy (referred to as PEG). In a conventional PEG procedure, the PEG tube is placed using endoscopic guidance or radiologic guidance.

During an exemplary PEG procedure, the PEG tube is placed into a patient's stomach using an endoscope to observe that the patient's esophagus is unobstructed and to inspect and inflate the stomach to ensure that the area selected for the gastrostomy tube may be extended. If the location is suitable, the area is selected for insertion of the gastrostomy tube. A needle is inserted into the area selected for the gastrostomy tube tract. An endoscopist will observe as the needle pushes through the patient's skin, through the abdominal wall, and into the gastric lumen in the selected area to form a needle tract. A guide wire is passed through the needle into the gastric lumen of the stomach. The endoscopist will use an endoscopic snare to grasp the guide wire firmly. The snare, passing through the working channel of the endoscope, firmly grabs the guide wire. Both the endoscope and snare are then withdrawn together through the patient's mouth, pulling the guide wire with the endoscope and snare. The end of the guide wire that extends out from the patient's mouth is subsequently attached to a retention element or device, and the other end of the guide wire remains outside the patient's skin in the abdominal region of the body. The retention element or device is guided back into the patient's mouth, without the endoscope, and pulled into the patient's stomach as the guide wire is pulled from the end that remains outside the patient's skin. The retention element or device is pulled snugly against the abdominal wall at the area selected from the gastrostomy tube. After suitable dilation of the needle tract, a gastrostomy tube is inserted into and through the tract while the stomach is held snugly against the abdominal wall by the retention element. The gastrostomy tube has a retainer on the distal end that may be expanded within the stomach after the distal end of the gastrostomy tube is inserted and properly placed.

Another exemplary PEG procedure involves placing an endoscope into the patient's mouth and advancing it along the esophagus into the stomach. The endoscope permits viewing the stomach lining to determine the correct insertion site of the gastrostomy tube, where a small incision is made in the abdominal wall. The procedure further involves inserting a guidewire and advancing the gastrostomy tube over the guidewire and through the patient's mouth, esophagus, stomach and out through the abdominal wall. The gastrostomy tube typically contains a retention means, both external and internal, to secure the tube in place and minimize accidental retraction and/or dislodgement.

There are several types of gastrostomy tubes of different sizes and having different internal retention means. Examples include a gastrostomy tube with internal mushroom-like soft and flexible bumper or bolster, a gastrostomy tubes with a semi-rigid internal bumper that prevents removal by external traction, and a balloon-retained gastrostomy tube where a balloon at the end of the tube positioned inside the stomach is inflated after insertion.

The insertion of gastrostomy tubes with a flexible or semi-rigid internal bumper is typically performed such that the end of the tube that is not engaged with the bumper is entered first, through the patient's mouth, and advanced along the guidewire and out the incision made in the abdominal wall until the retention bumper touches the internal wall of the stomach. The tube is then further secured using an external bolster affixed at the skin level.

Exemplary gastrostomy tubes are disclosed in U.S. Pat. No. 4,668,225 to Russo et al., U.S. Pat. No. 4,758,219 to Sacks et al., U.S. Pat. No. 5,080,650 to Hirsch et al., and U.S. Pat. No. 5,807,314 to Ross et al., the disclosures of which are hereby incorporated by reference.

Gastrostomy tubes need to be replaced regularly, typically every few months. Removal of the gastrostomy tube is performed by different methods, depending on the tube design. It is generally known that when a patient has had a gastrostomy tube for approximately two months, a durable passageway or tract is developed in the tissue through the abdomen and into the stomach, which will permit percutaneous reinsertion of a gastrostomy tube. As an example, a mushroom-retained tube may be removed by external traction. Upon pulling, the internal flexible bumper folds and slides out through the tube tract.

Another example of removal of the gastrostomy tube having a rigid internal bumper is to remove the internal bumper by endoscopic retrieval of the bumper via the esophagus and mouth. However, this method of gastrostomy tube removal is more complicated and costly since it involves repeat endoscopy and requires the patient to undergo surgical removal.

Another known method of gastrostomy tube removal involves a "cut and push" method, described in Kejariwal et al., 2009, *Nutr Clin Pract,* 24:281. This method is used with gastrostomy tubes having a rigid internal bumper and involves cutting the gastrostomy tube at the skin level and allowing the internal bumper and tube remnant to be expelled naturally. However, this method has several drawbacks, in that it may cause bowel obstruction and/or perforation.

Balloon-retained tubes are usually used when a tract has already been established in the abdominal wall. Such tubes may be inserted through the gastrostomy tube tract in a deflated form, and inflated when inside the stomach to secure the tube in place. Although simplistic to operate, such gastrostomy tubes are less durable and more prone to dislodgement.

Gastrostomy tubes often become dislodged or dislocated from the patient's body. If dislodgement or dislocation is discovered promptly, a simple percutaneous reinsertion of a new gastrostomy tube is possible, whereby the new gastrostomy tube is simply reinserted into the existing gastrostomy tube tract in the patient's abdomen and the balloon retention means reinflated. The reinsertion procedure may be performed by moderately-skilled medical personnel, such as nursing home staff or emergency room physicians, without the need for a medical doctor or surgeon.

Unfortunately, dislodging of the gastrostomy tube is usually not discovered promptly. Approximately two to three hours after dislodging, the gastrostomy tube tract in the patient's abdomen begins to close, making a simple percutaneous insertion impossible. Once the tract has closed, the involvement of a surgeon or gastroenterologist to surgically reinsert a gastrostomy tube is required. Often, admission to a hospital or medical facility is necessary to effect reinsertion of the gastrostomy tube.

There remains a need for improved means for reinserting a replacement gastrostomy tube into the abdominal tract without the need for additional surgery.

In addition, what is needed is an apparatus for dilating the collapsed soft tissue within the gastrostomy tube site for ease in reinserting a replacement gastrostomy tube.

Further, what is needed is method for progressive or sequential dilation of the tract that has closed due to the accidental dislodgement of the gastrostomy tube that eliminates the need for further surgery to open the gastrostomy tube tract.

There is a further need for improved means for reinsertion of a gastrostomy tube that permits a moderately-skilled health care provider, such as nursing home staff or emergency room physician, to quickly and easily dilate the collapsed soft tissue in the gastrostomy tube tract for purposes of reinserting a replacement gastrostomy tube.

SUMMARY

The present invention is directed to reinsertion means for gastrostomy tubes. The invention provides a means for dilation of the soft tissue of the tract or passageway for the gastrostomy tube once the tube is removed or dislodged from the patient.

In one aspect, the invention includes a plurality of dilators that permit progressive or sequential expansion of the tract of the gastrostomy tube.

In another aspect, the invention includes at least one dilator that is capable of separation and removal from the tract upon insertion of the gastrostomy tube into the hollow interior of the dilator.

In another aspect, the invention includes at least one dilator that is capable of being separated and removed from the tract once the gastrostomy tube has been reinserted in the tract of the abdominal wall, the gastric lumen, and into the stomach.

In yet another non-limiting aspect, the reinsertion device includes one dilator having a diameter of 3 mm and a rounded blunt tip, to ease open the collapsed soft tissue of the gastrostomy tube tract. The reinsertion device also includes a second dilator having a diameter of 5 mm and a rounded blunt tip, to further expand or open the tract of the gastrostomy tube. The reinsertion device also includes a third dilator having a diameter of 8 mm and a rounded blunt tip, having a hole in the distal end of the dilator, to further expand or open the tract of the gastrostomy tube, and for the insertion of the gastrostomy tube into the hollow interior of the third dilator and out through the opening in the distal end of the dilator. The third dilator further includes serrated sides for the removal of the sides of the dilator from the gastrostomy tube tract without removing the gastrostomy tube.

These and other aspects, objects, features, and advantages of the example embodiments will become apparent to those having ordinary skill in the art upon consideration of the following detailed description of illustrated example embodiments.

DRAWING ELEMENTS

Figure 1A:
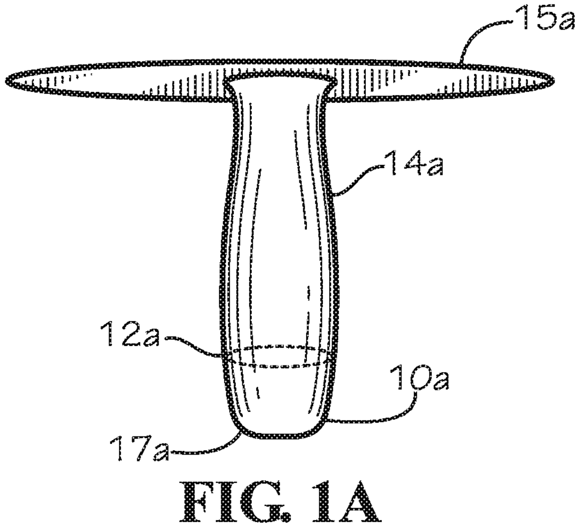
FIGS. 1A, 1B and 1C are views of one embodiment of three differently sized dilators of a gastrostomy reinsertion device.

| | |
|---|---|
| 10a | 3 mm diameter dilator |
| 10b | 5 mm diameter dilator |
| 10c | 8 mm diameter dilator |
| 11a | hollow interior of 3 mm diameter dilator |
| 11b | hollow interior of 5 mm diameter dilator |
| 11c | hollow interior of 8 mm diameter dilator |
| 12a | periphery of 3 mm diameter dilator |
| 12b | periphery of 5 mm diameter dilator |
| 12c | periphery of 8 mm diameter dilator |
| 14a | exterior wall of 3 mm diameter dilator |
| 14b | exterior wall of 5 mm diameter dilator |
| 14c | exterior wall of 8 mm diameter dilator |
| 15a | flange of 3 mm diameter dilator |
| 15b | flange of 5 mm diameter dilator |
| 15c | flange of 8 mm diameter dilator |
| 17a | rounded blunt tip of 3 mm diameter dilator |
| 17b | rounded blunt tip of 5 mm diameter dilator |
| 17c | rounded blunt tip of 8 mm diameter dilator with open end |
| 20 | opening in rounded blunt tip of 8 mm diameter dilator |
| 30 | gastrostomy tube |
| 33 | serrated sides of 8 mm diameter dilator |
| 35 | gastrostomy tube insertion site |

DETAILED DESCRIPTION OF THE EXAMPLE EMBODIMENTS

Overview

The present invention can be understood more readily by reference to the following detailed description, examples, drawings, and claims, and their previous and following description. However, before the present devices, methods and/or kits are disclosed and described, it is to be understood that this invention is not limited to the specific devices, methods and/or kits disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms “a,” “an,” and “the” comprise plural referents unless the context clearly dictates otherwise. Ranges can be expressed herein as from “about” one particular value, and/or to “about” another particular value. When such a range is expressed, another aspect comprises from the one particular value and/or to the other particular value. Similarly, when values are expressed as approximations, by use of the antecedent “about,” it will be understood that the particular value forms another aspect. It will be further understood that the endpoints of each of the ranges are significant both in relation to the other endpoint, and independently of the other endpoint.

In simplest terms, disclosed herein are gastrostomy tube reinsertion devices. In one aspect, the gastrostomy tube reinsertion devices disclosed herein comprise multiple dilators to open collapsed soft tissue from and within the gastrostomy tube tract in a progressive and sequential manner. The present invention provides a dilation device for dilating the gastrostomy tube tract in living tissues. Such device is useful for reinserting a gastrostomy tube into the tract in a human body, even after partial closure of the tract. Although the dilation device may be used for other purposes, it is discussed in the context of reinsertion of a gastrostomy tube. The present invention also provides the steps for reinserting a gastrostomy tube into a patient in need thereof.

The method described for replacement of gastrostomy tubes may be performed by moderately-skilled medical personnel, such as by an emergency room physician, without the need for surgery or a hospital stay, which will reduce the costs to the patient and/or the patient’s insurer.

Figure 1B:
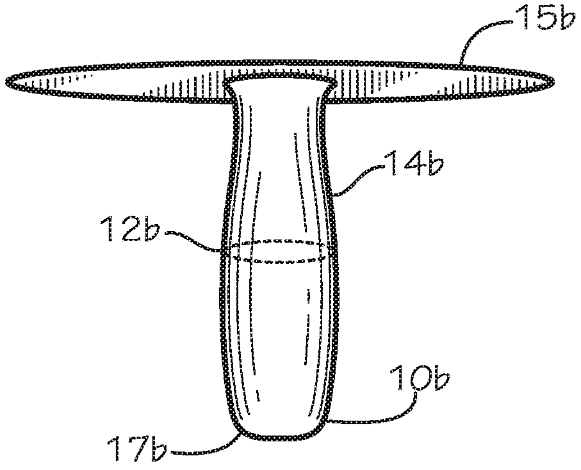
Figure 1C:
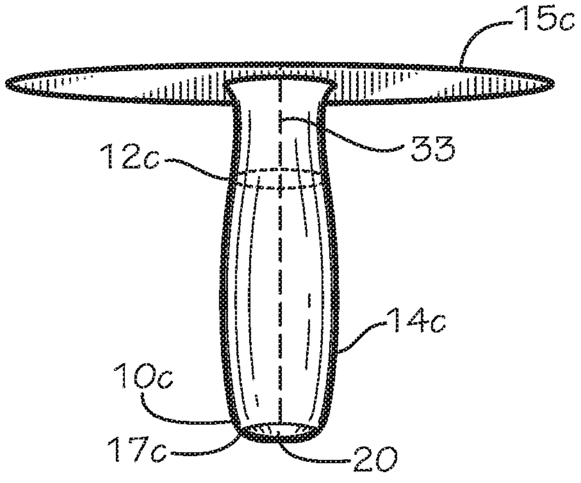

Referring to FIGS. 1A, 1B and 1C, the dilators 10*a*, 10*b*, 10*c* are in incremental sizes. The first dilator 10*a* is hollow 11*a* with an outer surface 12*a* having a defined periphery of 3 mm and a length of 5 cm. The exterior wall 14*a* of the first dilator 10*a* is 1 mm thick and has a flange 15*a* at the top that is 3 cm in diameter and 2 mm in thickness. The function of the flange 15*a* is to prevent accidental insertion of the first dilator 10*a* completely into the stomach. The first dilator 10*a* has a rounded blunt tip 17*a* at the distal end of the dilator 10*a*. The function of the rounded blunt tip 17*a* is to gently ease apart the collapsed soft tissue of the gastrostomy tube insertion site 35 and the gastrostomy tube tract.

The second dilator 10*b* is hollow 11*b* with an outer surface 12*b* having a defined periphery of 5 mm and a length of 5 cm. The exterior wall 14*b* of the second dilator 10*b* is 1 mm thick and has a flange 15*b* at the top that is 3 cm in diameter and 2 mm in thickness. The function of the flange 15*b* is to prevent complete insertion of the second dilator 10*b* into the stomach. The second dilator 10*b* has a rounded blunt tip 17*b* at the distal end of the second dilator 10*b*. The function of the rounded blunt tip 17*b* of the second dilator 10*b* is to further gently ease apart the collapsed soft tissue of the gastrostomy tube insertion site 35 and the gastrostomy tube tract.

The third dilator 10*c* is hollow 11*c* with an outer surface 12*c* having a defined periphery of 8 mm and a length of 5 cm. The exterior wall 14*c* of the third dilator 10*c* is 1 mm thick and has a flange 15*c* at the top that is 3 cm in diameter and 2 mm in thickness. The function of the flange 15*c* is to prevent accidental insertion of the third dilator 10*c* completely into the stomach. The third dilator 10*c* has a rounded blunt tip 17*c* that includes an opening 20 in the bottom of the tip to permit insertion of the replacement gastrostomy tube 30. The third dilator 10*c* is serrated 33 on both sides to allow for separation and removal after the replacement gastrostomy tube 30 is placed through the third dilator 10*c*.

A view of one embodiment of the dilation device is illustrated. In one aspect, the dilation device comprises three differently sized dilators 10*a*, 10*b*, 10*c*. As one skilled in the art will appreciate, the dilators 10*a*, 10*b*, 10*c* can be of any size as long as adequate for the assigned task, that being the dilation of collapsed soft tissue of the gastrostomy tube site 35 and the gastrostomy tube tract.

In one aspect, the first and second dilators 10*a*, 10*b* are defined by an open end port on the top surface of the flange 15*a*, 15*b* and a closed end on the bottom rounded blunt tip 17*a*, 17*b*. The flange 15*a*, 15*b* is placed at the top of the dilator 10*a*, 10*b* for the purpose of preventing the dilator 10*a*, 10*b* from being inserted completely into the stomach. It is also contemplated that the third dilator 10*c* can be open at both ends and, in this aspect, the open ends of the dilator 10*c* are defined in the respective top and bottom surfaces of the dilator 10*c*.

Each dilator 10*a*, 10*b*, 10*c* is made of a firm, yet flexible material, such as silicone. Each dilator 10*a*, 10*b*, 10*c* defines a respective outer surface 12*a*, 12*b*, 10*c* having a respective periphery of differing sizes. Each dilator 10*a*, 10*b*, 10*c* also defines a tapering rounded blunt tip end 17*a*, 17*b*, 10*c*.

The plurality of dilators 10*a*, 10*b*, 10*c* have peripheries of various dimensions so that a set of dilators may be used as serial dilators. By using the plurality of dilators 10*a*, 10*b*, 10*c* in sequence from smaller to larger periphery, the gastrostomy tube tract is gradually dilated. For a dilator suitable for a gastrostomy tube reinsertion, the largest dilator should have a periphery approximately as large as the periphery of the gastrostomy tube and, preferably, approximately 1-2 mm larger than the gastrostomy tube. Each dilator is preferably about 3-7 cm in length and most preferably 5 cm in length.

The process of dilating the tract or passageway for the purpose of reinserting a replacement gastrostomy tube 30 is as follows. First, the exterior surfaces of each dilator 10*a*, 10*b*, 10*c* are lubricated with a water-soluble lubricant such as K-Y gel. The area of the gastrostomy tube site 35 should be cleaned with suitable cleansing products and dried prior to insertion of the replacement gastrostomy tube 30. The lubricated dilator 10*a* having the smallest periphery is inserted gently into the gastrostomy tube site 35 and advanced slowly and gently through the soft tissue of the tract until the flange 15*a* of the dilator 10*a* reaches the skin of the abdomen. The dilator 10*a* is then slowly and gently removed and the second dilator 10*b* having a larger periphery is immediately inserted into the partially dilated gastrostomy tube site 35 and advanced gently and slowly through the same soft tissue of the tract until the flange 15*b* of the dilator 10*b* reaches the abdominal skin. The dilator 10*b* is gently removed and the third and final dilator 10*c* having a periphery larger than the second dilator 10*b* is immediately inserted into the partially dilated tract and advanced slowly and gently through the same soft tissue of the tract until the flange 15*c* of the dilator 10*c* reaches the abdominal skin. The replacement gastrostomy tube 30 is lubricated with a lubricant such as K-Y gel and inserted into the hollow interior 11*c* of the third dilator 10*c* and through the bottom open end 17*c* of the dilator 10*c*. Once the replacement gastrostomy tube 30 has been placed sufficiently through the dilator 10*c*, the flange 15*c* of the dilator 10*c* is lifted up from the abdominal skin and the dilator 10*c* is separated along the serration 33 and removed from the gastrostomy tube tract. The gastrostomy tube 30 remains in the tract and into the stomach where the balloon at the end of the gastrostomy tube 30 is inflated and the placement inside the stomach is confirmed.

The placement of the gastrostomy tube 30 may be confirmed via radiography to visualize placement of the gastrostomy tube 30. Another means of confirming the placement of the gastrostomy tube 30 is by aspirating gastric contents via the gastrostomy tube 30 and measuring the pH of the aspirate.

Figure 2:
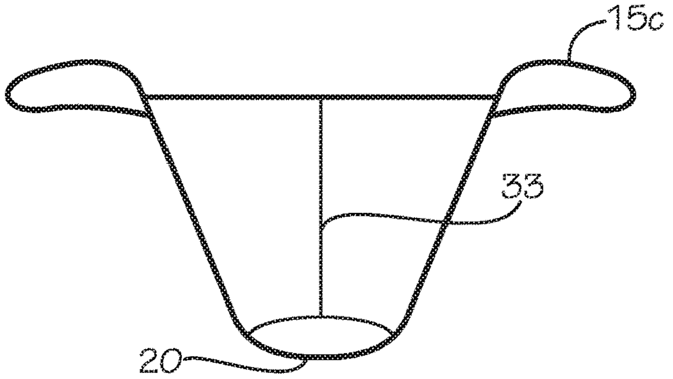
FIG. 2 is a side view of the dilator of a gastrostomy tube reinsertion device having serrated walls.

Referring to FIG. 2, the serrated walls of the third dilator 10*c* are shown in a locked position outside the patient's body. After the third and final dilator 10*c* having a periphery larger than the second dilator 10*b* is inserted into the partially dilated tract and advanced slowly and gently through the same soft tissue of the tract until the flange 15*c* of the dilator 10*c* reaches the abdominal skin, the replacement gastrostomy tube 30 is then advanced through the opening at the top of the hollow dilator 10*c* and through the hollow dilator and out of the opening at the bottom of the dilator 10*c* into the stomach, then the flanges 15*c* of the third hollow dilator 10*c* are lifted up from the abdominal skin and gently pulled apart so as to separate along the serration 33 and removed from the gastrostomy tube tract.

Figure 3:
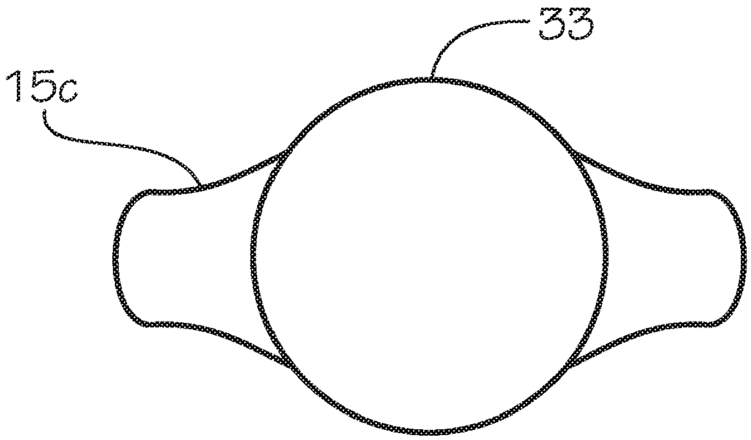
FIG. 3 is a top view of a dilator of the gastrostomy tube reinsertion device depicting the hollow interior and the flanges of the dilator.
Figure 4:
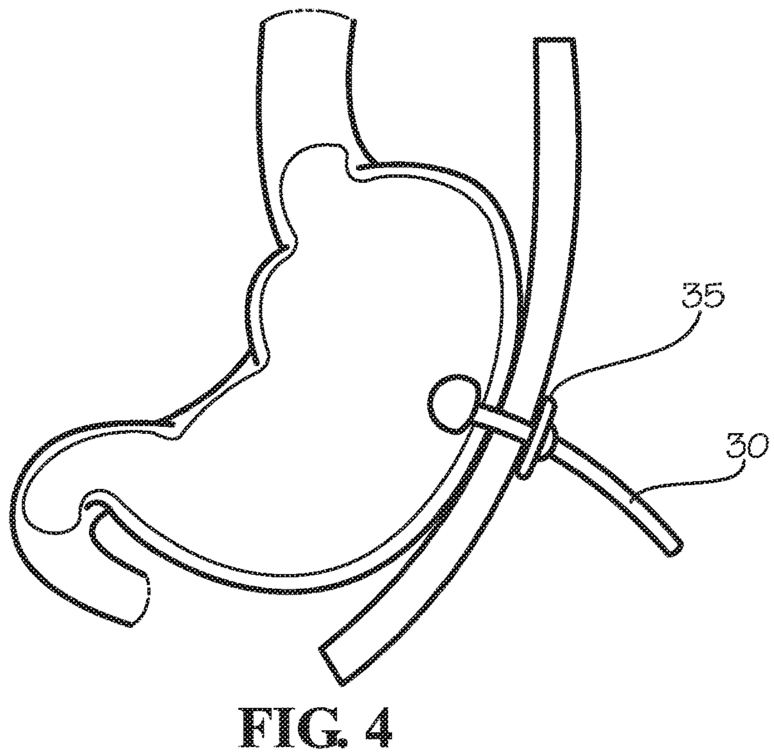
FIG. 4 is a schematic illustration of a gastrostomy tube placed through the abdominal wall and into the gastric lumen of the stomach.

Referring to FIG. 3, depicting a top view of the third hollow dilator 10*c* with its serrated sides 33, the removal of the third hollow dilator 10*c* does not occur until after the gastrostomy tube 30 has been inserted into the open end at the top of the dilator 10*c* and advanced through the hollow interior 11*c* of the dilator 10*c* and out through the bottom opening 20.

In another aspect of the invention, the balloon retention device of the gastrostomy tube 30 may be inflated prior to removal of the hollow dilator 10*c* in order to prevent the gastrostomy tube 30 from retracting back into the hollow dilator 10*c*. After inflation of the balloon retention means of the gastrostomy tube 30, the flanges 15*c* of the hollow dilator 10*c* are lifted up from the abdominal skin and gently pulled apart so as to separate along the serration 33 and removed from the gastrostomy tube tract. The gastrostomy tube 30 remains in the tract and into the stomach, and the placement of the gastrostomy tube inside the stomach is confirmed by radiology or other verification practice means.

The dilation device disclosed herein may many uses known to those of skill in the art. For example, the disclosed dilation device can be used in any living tissue having a collapsed soft tissue site.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A dilation gastrostomy tube reinsertion device for progressive dilation of a gastrostomy tube tract in living tissue of a mammalian body comprising:

a first dilator having a flange to prevent complete insertion of the first dilator into the body, an outer surface having a periphery, and a closed distal end, the closed distal end having a rounded blunt tip;

a second dilator being separate and independent of the first dilator and having a flange to prevent complete insertion of the second dilator into the body, an outer surface having a periphery greater than said periphery of the first dilator, and a closed distal end, the closed distal end having a rounded blunt tip; and a third dilator being separate and independent of the first dilator and second dilator and having a hollow interior and a flange to prevent complete insertion of the dilator into the body, an outer surface having a periphery greater than the peripheries of the first and second dilators, an open distal end having a rounded blunt tip with an opening sufficient to allow a gastrostomy tube to pass through the rounded blunt tip, and serrated edges extending from the open distal end to the flange on two sides of the third dilator to allow for separation.

2. The device of claim 1, wherein the first dilator is 3 mm in diameter, the second dilator is 5 mm in diameter, and the third dilator is 8 mm in diameter.

3. The device of claim 1, wherein each flange is 3 cm in length and 2 mm thick.

4. The device of claim 1, wherein each dilator is between approximately 3 cm and 5 cm in length.

5. The device of claim 1, wherein each dilator is 5 cm in length.

6. The device of claim 1, wherein the wall of each dilator is approximately 1 mm in thickness.

7. The device of claim 1, wherein each dilator is a flexible silicone product.

8. A gastrostomy tube reinsertion kit comprising:

a first dilator having a flange to prevent complete insertion of the dilator into the body, an outer surface having a periphery, and a closed distal end, the closed distal end having a tapered rounded blunt tip;

a second dilator being separate and independent of the first dilator and having a flange to prevent complete insertion of the dilator into the body, an outer surface having a periphery greater than said periphery of the first dilator, and a closed distal end, the closed distal end having a tapered rounded blunt tip; and a third dilator being separate and independent of the first dilator and second dilator and having a hollow interior and a flange to prevent complete insertion of the dilator into the body, an outer surface having a periphery greater than said periphery of the first and second dilators, an open distal end having a rounded blunt tip with an opening sufficient to allow a gastrostomy tube to pass through the rounded blunt tip, and serrated edges extending from the open distal end to the flange on two sides of the third dilator to allow for separation.

9. The gastrostomy tube reinsertion kit of claim 8, further comprising a gastrostomy tube.

* * * * *